(12) United States Patent
Hintzer et al.

(10) Patent No.: US 6,703,520 B2
(45) Date of Patent: Mar. 9, 2004

(54) PROCESS OF PREPARING HALOGENATED ESTERS

(75) Inventors: Klaus Hintzer, Kastl (DE); Egon Obermaier, Taubenbach (DE); Werner Schwertfeger, Altötting (DE)

(73) Assignee: 3M Innovative Properties Company, St. Paul, MN (US)

( * ) Notice: Subject to any disclaimer, the term of this patent is extended or adjusted under 35 U.S.C. 154(b) by 36 days.

(21) Appl. No.: 10/117,241

(22) Filed: Apr. 5, 2002

(65) Prior Publication Data

US 2002/0177729 A1 Nov. 28, 2002

(30) Foreign Application Priority Data

Apr. 24, 2001 (EP) ............................................. 01201473

(51) Int. Cl.$^7$ ....................... C07C 205/00; C07C 69/63; C07C 43/00
(52) U.S. Cl. ..................... 560/125; 560/226; 568/687
(58) Field of Search ................................. 560/123, 124, 560/129, 226, 227, 125; 568/687

(56) References Cited

U.S. PATENT DOCUMENTS

| | | |
|---|---|---|
| 2,713,593 A | 7/1955 | Brico et al. |
| 2,988,537 A | 6/1961 | Wiley |
| 3,291,843 A | 12/1966 | Fritz et al. |
| 4,523,039 A | 6/1985 | Lagow et al. |
| 4,526,948 A | 7/1985 | Resnick |
| 4,766,248 A * | 8/1988 | Krespan ..................... 568/31 |
| 4,859,747 A | 8/1989 | Bierschenk et al. |
| 5,235,094 A | 8/1993 | Darst et al. |
| 5,466,877 A | 11/1995 | Moore |
| 5,488,142 A | 1/1996 | Fall et al. |

OTHER PUBLICATIONS

*Modern Fluoropolymers*, John Scheirs, Wiley Series in Polymer Science, 1997, pp. 377–378.
*Russian Journal of Organic Chemistry*, vol. 30, No. 8, 1994, "Copolymerization of Perfluorooxaalkyl Allyl Ethers", Emel 'yanov et al, pp. 1266–1270.

*Kirk Othmer Encyclopedia of Chemical Technology*, 3$^{rd}$ Edition, V. 10, p. 636 "Fluorine"; pp. 840–855 "Direct Fluorination", John Wiley & Son, Inc., New York, New York, 1980.

Lagow et al, "Progress In Inorganic Chemistry", vol. 26, pp. 161–210 (1979).

*Angewandte Chemie, English Edition*, vol. 24, 1985, H. Millauer et al, "Hexafluoropropene Oxide–a Key Compound in Organofluorine Chemistry", pp. 161–179.

* cited by examiner

Primary Examiner—Porfirio Nazario-Gonzalez
Assistant Examiner—Karl J. Puttlitz
(74) Attorney, Agent, or Firm—James V. Lilly; Brian E. Szymanski

(57) ABSTRACT

The present invention provides a process for preparing a desired halogenated ester, which process comprises the steps of:

(a) contacting (A) a substantially organic solvent free liquid mixture of (i) an alkanolate of the formula M—O—Z, wherein M is an alkali or alkaline earth metal, and Z is a linear, branched or cyclic alkyl group of 1 to 10 carbon atoms and (ii) a diester with (B) a halogenated ethylenically unsaturated olefin at a temperature of not more than 40° C. and with a mol ratio of halogenated ethylenically unsaturated olefin to alkanolate of not more than 1.1;

(b) contacting an acid with a thus obtained reaction mixture thereby obtaining a mixture comprising the desired halogenated ester; and (c) recovering the halogenated ester from said reaction mixture.

In step (a) of the process, the mixture of the alkanolate and diester is contacted with the halogenated ethylenically unsaturated olefin under conditions of agitation sufficient such that the weight ratio of halogenated ester to halogenated ketone as a byproduct obtained after step (b) is at least 10:1.

10 Claims, No Drawings

PROCESS OF PREPARING HALOGENATED ESTERS

CLAIM OF PRIORITY

This application claims priority from European Patent Application No. 01201473.4 filed Apr. 24, 2001.

1. Field of the Invention

The present invention relates to a process for making halogenated esters such as for example methyl-3-methoxytetrafluoropropanoate. In particular, the present invention relates to a process of making such halogenated esters wherein the process can be run under more environmental friendly conditions and in an economically feasible way.

2. Background of the Invention

Halogenated esters such as for example methyl-3-methoxytetrafluoropropanoate are typically used in the preparation of halogenated vinyl ethers, in particular in the preparation of certain perfluorinated or partially fluorinated vinyl ethers. Such fluorinated vinyl ethers may be used in the manufacture of fluoropolymers, in particular in the manufacture of fluoropolymers including fluorinated ion exchange resins, fluoroelastomers and fluorothermoplasts that have desirable properties. Some of the benefits of employing vinyl ethers in fluoropolymers are described in various review articles. See for example, Modern Fluoropolymers, John Scheirs, Wiley Series in Polymer Science, 1997. See also Emel 'yanov et al, Zh. Org. Khim (1994), 30(8), 1266–70.

There are a number of routes to prepare fluorinated vinyl ethers. Generally these routes start with (per)fluorinated acid fluorides. See for example Modern Fluoropolymers, J. Scheirs, Wiley Series in Polymer Science, 1997 and the literature cited therein. These (per)fluorinated acid fluorides may for example be prepared from the fluorination of halogenated esters.

Processes for producing halogenated esters are already known. One such process is described in U.S. Pat. No. 2,988,537. However, the yields of the halogenated ester produced according to the process disclosed in this US-patent appear to be low and further the amounts of halogenated ketone byproduct are high. Although it is taught in this patent to generally conduct the first step in the reaction sequence in an organic solvent, there is also an example disclosing a process in which no organic solvent is used in the initial step. In this particular example, tetrafluoroethylene is added to a mixture of sodium methoxide and dimethyl carbonate at a temperature of 40° C. Subsequent thereto, the resulting mixture is taken up in ether as an organic solvent and acidified with sulfuric acid. According to the results disclosed, only 17% yield of the halogenated ester is obtained together with about 75% yield of the halogenated ketone. It thus appears that under the conditions of this example, the formation of halogenated ketone is preferred over that of the halogenated ester.

U.S. Pat. No. 5,235,094 describes a process designed to maximize the yield of halogenated ester while keeping the amount of the halogenated ketone as a byproduct as low as possible. According to U.S. Pat. No. 5,235,094, the halogenated esters are produced by contacting a mixture of an alkanolate and a diester in an organic solvent with a halogenated, ethylenically unsaturated olefin at a temperature of not more than 15° C. Further, it is taught that the mole ratio of the olefin to the alkanolate should be between 0.89 mole and 0.99 mole. Although the process disclosed in this US-patent can yield the desired halogenated ester in high amounts with a low amount of contamination with undesired halogenated ketone byproduct, the process has some disadvantages. For example, it appears that the process needs to be run under fairly strict conditions in order to achieve the high yields and to minimize the amount of byproduct. In particular, it appears that the temperature needs to be controlled carefully well below room temperature. Another important factor to control is the mole ratio of olefin to alkanolate. As can be seen from the examples, it is critical in the prior art process that the mole ratio of olefin to alkanolate is controlled carefully to just below the stoichiometric amount. This implies that the amount and purity of the reactants used need to be carefully controlled. Additionally, it is taught that the process should be run in very dry conditions to achieve a high yield of desired product. Finally, the use of organic solvent in the process presents environmental problems and may make the recycling of excess diester and solvent used in the reaction difficult. Recycling of excess diester and the solvent is complicated by the formation of equimolar amounts of alcohol in the acidification step.

Accordingly, it is now a desire to find an alternative process for making a halogenated ester in high yield and with a minimal amount of byproduct while avoiding some disadvantages of the prior art. For example, it would be desirable to find a process which is more convenient and flexible for use on an industrial scale. In particular, it would be desirable to develop a process which is less dependent on the purity levels of the reactants used. Additionally, it would be desirable to find a process in which recycling of unused diester can be practiced more efficiently and which process is more friendly from an environmental point of view.

SUMMARY OF THE INVENTION

The present invention provides a process for preparing a desired halogenated ester, which process comprises the steps of:

(a) contacting (A) a substantially organic solvent free liquid mixture of (i) an alkanolate of the formula M—O—Z, wherein M is an alkali or alkaline earth metal, and Z is a linear, branched or cyclic alkyl group of 1 to 10 carbon atoms and (ii) a diester with (B) a halogenated ethylenically unsaturated olefin at a temperature of not more than 40° C. and with a mol ratio of halogenated ethylenically unsaturated olefin to alkanolate of not more than 1.1;

(b) contacting an acid with a thus obtained reaction mixture thereby obtaining a mixture comprising the desired halogenated ester; and (c) recovering the halogenated ester from said reaction mixture.

In step (a) of the process, the mixture of the alkanolate and diester is contacted with the halogenated ethylenically unsaturated olefin under conditions of agitation sufficient such that the weight ratio of halogenated ester to halogenated ketone as a byproduct obtained after step (b) is at least 10:1.

By the term "substantially organic solvent free" is meant that no organic solvent is added to carry out the reaction. However, the term should not be interpreted to mean that all organic solvents are excluded from the reaction. In particular, organic solvents may be present as part of a minor contamination (e.g. upto 1% by weight) of one or more reactants.

By the term "liquid mixture" is meant that the mixture should generally be liquid under the conditions at which the reaction is being carried out such that the mixture can be stirred. "Liquid mixture" in particular covers any stirrable mixture including solids free liquid, slurry in which some solid may be present, up to pasty like mixtures with high viscosity.

The process of the invention has the advantage that the reaction can be carried out without the need for the addition of organic solvents. In particular, steps (a) through (c) of the process can be conducted without using organic solvent. This makes recycling of reactants more easy. For example, the diester which is generally used in an excess amount in the reaction can be more easily recovered after the reaction. Also, the recovered diester can be reused in a subsequent run of the process. Furthermore, because no organic solvent is used, the process is also more environmentally friendly.

Further, despite the fact that no organic solvent is used, the process of the present invention can yield the desired halogenated ester in high amounts with minimal amounts of halogenated ketone byproduct. Also, in achieving these results, the process of the invention is less critical and less dependent on such factors as the exact reaction conditions and purity levels of the reactants used. For example, the process is generally less temperature dependent, a slight amount of olefinic reactant in excess of its stoichiometric amount can be tolerated and there is no need to handle the reactants under extremely dry conditions. Accordingly, the process of the present invention is generally more convenient to practice and more feasible from an economical point of view.

DETAILED DESCRIPTION OF THE INVENTION

In accordance with an embodiment of the present invention, a liquid mixture of the alkanolate and diester, such as a carbonate ester, is prepared and charged in a reactor, for example a stainless steel or glass lined reactor. An example of a liquid mixture is a mixture of a methanolate, e.g. sodium methanolate, and dimethyl carbonate. Such a mixture will generally be liquid at a temperature of at least 4° C. No organic solvent is used to prepare the liquid mixture. As the reaction is preferably carried out in an inert atmosphere, the reactor is generally flushed with nitrogen and the reactor may subsequently be evacuated.

The halogenated ethylenically unsaturated olefin, e.g. tetrafluoroethylene, is then metered into the reactor and added to the liquid mixture of alkanolate and diester while stirring or otherwise agitating the liquid mixture. To achieve the desired high ratio of halogenated ester to halogenated ketone of at least 10:1, the liquid mixture should be sufficiently agitated or stirred so that a good transfer of olefin into the liquid mixture can be assured. The olefin may be added to the gas phase as well as directly into the liquid mixture. Stirring conditions suitable for use in the process are dependent on the way of addition of the olefin (to the gas phase or liquid mixture), geometry of the reactor, i.e. combination of mixer and baffles. Suitable mixing systems are described in Rührtechnik, H. P. Wilke et al., Hüthig Verlag, Heidelberg, 1988. A simple anchor or impeller mixer may be used when the olefin is added directly to the liquid mixture. A hollow shaft mixer may be used when the olefin is added to the gas phase. The optimal stirring conditions can be readily determined by one skilled in the art through routine experimentation.

The reaction temperature during the addition of the halogenated ethylenically unsaturated olefin is not so critical in the process of the invention but should generally not exceed 40° C. Subsequent to the completion of the addition of the halogenated ethylenically unsaturated olefin, the reaction is usually allowed to continue for up to about 6 hours after which the reaction of step (a) of the process is generally completed.

In the second step of the process, the pH of the reaction mixture is lowered by addition thereto with agitation of an acid. The temperature during this second step of the process is preferably between 10 and 60° C.

After completion of the second step of the process, a mixture of the desired halogenated ester is obtained which is generally accompanied with ketone byproduct. The desired halogenated ester is recovered by conventional means such as removing the salt in a filter, centrifuge or aqueous wash, and then distilling the solids free reaction mixture. The ketone byproduct is, of course, passed through these recovery steps along with the ester product.

The reactants described above are generally used in the process of this invention in number of moles per mole of alkanolate as follows:

(i) halogenated olefin: not more than 1.1, preferably between 0.9 and 1.1;

(ii) diester: about 2.0 to about 4.0, and preferably about 2.5 to about 3.5;

(iv) and acid: about 1.0. If a weak acid like formic or acetic acid is used, up to 1.5 moles may be used.

Suitable alkanolates for use in the process of the invention are described by the formula M—O—Z, where M is an alkali metal such as lithium, sodium, potassium or cesium or an alkaline earth metal such as magnesium or calcium; and Z is a linear, branched or cyclic alkyl group containing 1 to 10 carbon atoms, preferably 1 to 6 carbon atoms, and more preferably 1–4 carbon atoms. The group Z may optionally contain halogen (such as chlorine, fluorine or bromine) substituents. Representative examples of Z include methyl, ethyl, isopropyl, isobutyl, isopentyl, neopentyl, pentyl, cyclopentyl, hexyl, cyclohexyl, octyl, cyclooctyl, nonyl, decyl radicals, and the like, each optionally containing halogen substituents. An example of a preferred alkanolate is sodium methoxide (sodium methylate). Sodium methoxide is commercially available or may be made, for example, by either reacting molten sodium with methanol or by reacting methanol with sodium amalgam obtained from the electrolysis of brine.

Halogenated olefin compounds which may be advantageously used for addition to a diester in the process of this invention can be described generally by the formula $CX_2=CX_2$, where each X is independently hydrogen, fluorine, chlorine, bromine or iodine, provided that at least one X must be fluorine. An example of a preferred halogenated olefin is tetrafluoroethylene, which may be made by reacting hydrogen fluoride and chloroform to give chlorodifluoromethane, which is then pyrolyzed in a non-catalytic gas-phase reaction at atmospheric or reduced pressure, usually at about 590° C.–900° C.

Representative diesters which are useful in the process of this invention may include carbonate esters (carbonic acid esters) such as those described generally by the formula:

ROOCOR    (II)

where each R is independently a linear, branched or cyclic alkyl or alkylene radical, or an aryl or arylene radical, containing 1 to 18 carbon atoms, preferably 1–10 carbon atoms, and more preferably 1 to 6 carbon atoms, and optionally containing halogen (such as chlorine, fluorine or bromine) substituents. Representative examples of R include methyl, ethyl, isopropyl, isobutyl, isopentyl, neopentyl, pentyl, cyclopentyl, hexyl, cyclohexyl, octyl, cyclooctyl, nonyl, decyl, benzyl, tolyl, xylyl and naphthyl radicals, and the like, each optionally containing halogen substituents. An example of a preferred diester is dimethylcarbonate (where each R is methyl), which is available commercially or may be prepared by reacting carbon monoxide, oxygen and methanol at about 90° C. and about 10 MPa or less, using a cuprous chloride catalyst.

For performing the second step of the process, organic acids such as acetic, formic or propionic acid can be used as well as mineral acids such as hydrochloric, hydrofluoric, sulfuric, phosphoric, hydrobromic, sulfonic, or nitric acid, and the like.

The desired ester product formed from the reactants described above may be described by the following formula:

Z—OCX$_2$—CX$_2$—COOR    (III)

where R, X and Z are as set forth above.

As a particular example, when tetrafluoroethylene is added to a liquid mixture of sodium methoxide and dimethyl carbonate, and the resulting intermediates are neutralized with HCl, the material contained in the reaction mixture, after removal of the salt waste, is a mixture of the desired ester product methyl 3-methoxyperfluoropropanoate, and the ketone byproduct di-2-methoxyperfluoroethylketone.

The resulting ester products of formula (III) wherein X is fluorine obtained with the process of the invention are advantageously used to produce products of the following formula:

R$_f$OCF$_2$CF$_2$COF    (IV)

wherein R$_f$ is a perfluoroaliphatic group of 1 to 10 carbon atoms, preferably 1 to 3 carbon atoms.

The products of formula (IV) can be produced by fluorinating the ester products of formula (III) by contacting the ester product with a fluorinating agent under conditions sufficient to replace the hydrogen atoms on the ester product with fluorine and if needed converting the resulting product to the perfluorinated acid fluoride.

The fluorination is done under conditions that are appropriate to replace the hydrogen on the starting material, but not so aggressive that backbone of the starting material is disturbed. Fluorination can be accomplished by a number of techniques. Examples of useful fluorination techniques include electrochemical fluorination (ECF) and direct fluorination (DF).

Electrochemical fluorination is a well known technique that is disclosed in a number of publications including U.S. Pat. No. 2,713,593 and WO 98/50603. It is a process that employs hydrogen fluoride. Electrochemical fluorination of the ester products results directly in the desired perfluorinated acid fluoride. As a result, there is no need to convert the product of this step any further.

Direct fluorination is another well known technique. This technique is disclosed in a host of articles and patents. See for example, U.S. Pat. No. 5,488,142 (Fall et al); U.S. Pat. No. 4,523,039 (Lagow et al); Kirk Othmer Encyclopedia of Chemical Technology, 3rd Edition, V. 10, pp 636, 840–855, John Wiley & Sons, Inc., New York, N.Y. (1980); Lagow et al, Progress in Inorganic Chemistry, 26, 161–210 (1979); U.S. Pat. No. 4,859,747 (Bierschenk et al).

During direct fluorination, fluorine, which may be diluted with an inert liquid or gas, and the ester products are contacted in an appropriate vessel (e.g., either a stirred tank reactor or a tubular reactor). The amounts of each are selected to have a stoichiometric excess of fluorine. Fluorination is allowed to take place for a time sufficient to replace all of the hydrogens on the precursor with fluorine.

Direct fluorination of the ester products of formula (III) is preferably carried out in the presence of an unfluorinated coreactant. The coreactant is often selected from certain common organic solvents. Preferably, the coreactant provides a source of reactive hydrogen that initiates free radical chain reactions between the starting material and the fluorinating agent. Preferred unfluorinated reactants are non-chlorinated, non-hydroxylic compounds. Most preferably they are ethers. Low molecular weight materials (e.g., weight average molecular weight of 150 or less) are the most preferred.

Examples of unfluorinated reactants that are useful in the practice of the direct fluorination include polar, aprotic compounds and nonpolar, aprotic compounds. Representative examples of polar, aprotic compounds include hydrocarbon esters, acyclic ethers such as diethyl ether, ethylene glycol dimethyl ether, and diethylene glycol dimethyl ether; cyclic ethers such as tetrahydrofuran, 2-methyltetrahydrofuran, dioxane, dioxolane, and 4-methyldioxolane; ketones such as acetone and 2-butanone; carboxylic acid esters such as methyl formate, ethyl formate, methyl acetate, diethyl carbonate, propylene carbonate, ethylene carbonate, and butyrolactones. Mixtures of polar aprotic compounds may be used if desired. Representative examples of useful nonpolar, aprotic compounds include toluene, benzene, hexane, heptane and the like. Mixtures of nonpolar, aprotic compounds may be used if desired. If desired, polar, aprotic compounds can be mixed with nonpolar, aprotic compounds. Factors involved in the selection include compatability of the unfluorinated reactants with the ester product to be fluorinated and ease of separation of perfluorinated products.

The unfluorinated coreactants and the ester product of formula (III) are preferably simultaneously fed to the fluorination vessel. As little as 10% by weight of the coreactant has a beneficial effect upon yield. Direct fluorination of the ester product results in the formation of a fluorinated intermediate which is then converted to the perfluorinated acid fluoride by techniques known to the art. For example, the intermediate can be converted to the acid fluoride as is described in U.S. Pat. No. 5,466,877 (Moore). Other techniques are, of course, also useful in this conversion.

The perfluorinated acid fluoride of formula (IV) is advantageously used to produce perfluorovinyl ethers. For example, $CF_3-OCF_2CF_2CF_2O-CF_2=CF_2$ may be produced from $CF_3-O-CF_2CF_2COF$ as follows: In the first step, the acid fluoride is reacted with hexafluoropropene oxide (HFPO) in the presence of a suitable catalyst. This conversion is described in H. Millauer et al, Angewandte Chemie, English Edition, 24, 161 (1985). The monoaddition product is preferably converted to the potassium or sodium salt which is pyrolysed resulting in the vinyl ether e.g. according to U.S. Pat. No. 3,291,843. This reaction sequence is illustrated by the following equations.

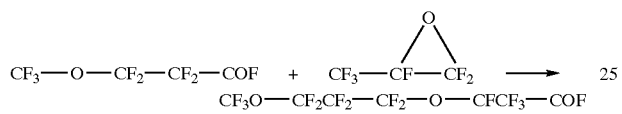

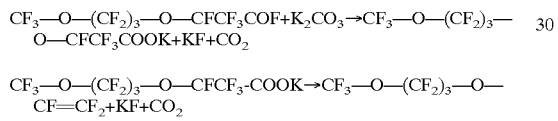

The following examples will further illustrate the invention without however the intention to limit the invention thereto.

EXAMPLE 1

A liquid mixture of 12.55 kg (232.5 mole) of sodium methoxide and 62.5 (693.8 mole) dimethylcarbonate was provided in a stainless steel reactor. The reactor was flushed with nitrogen until all oxygen was replaced with nitrogen and subsequently the reactor was evacuated. Tetrafluoroethylene (TFE) was then added into the liquid mixture while vigorously stirring the reaction mixture with an anchor mixer and maintaining a temperature of 10° C. The maximum TFE partial pressure was 1.2 bar. During a period of 4 hours and 40 minutes, 23.25 kg (232.5 mole) of TFE were added. The reaction was then allowed to continue for 3 hours whereby TFE was fully consumed. Subsequently, 16.56 kg (275.8 mole) of glacial acetic acid were pumped into the reactor vessel. The mixture was then stirred for 2 hours at 40° C. and then 80 liters of water were added. After all salt had been dissolved, the organic phase was separated. A gaschromatogram of the organic phase showed a weight ratio of ester to ketone of 17:1. The ester could be recovered from the organic phase by distillation resulting in a yield of the ester of 80.7%.

EXAMPLE 2

Using the same procedure as described in example 1, 69.75 kg of sodium methoxide and 364.3 kg of dimethyl carbonate were converted with 131 kg of TFE. An impeller mixer was used and the olefin was added to the liquid phase. The internal temperature was held in the range of 10 to 35° C. and the partial pressure of TFE was 1.5 bar. After 4 h 25 min the TFE addition was complete. After a post reaction time of 2 h all of the TFE was consumed. 92.5 kg of glacial acetic acid was added at 10 to 15° C. over a period of 1 h. The mixture was heated to 40° C. and stirred for additional 2 h. Water was added until all of the salt was in solution and the lower phase was separated and analyzed by GC. The ester/ketone ratio was 15.1:1.

EXAMPLES 3 and 4

Example 2 was repeated. Reaction conditions and results are listed in the following table.

|  | Example 3 | Example 4 |
|---|---|---|
| $CH_3ONa$ | 70.1 kg | 70 kg |
| $CH_3OCOOCH_3$ | 346 kg | 346 kg |
| $CF_2=CF_2$ amount | 131 kg | 131 kg |
| partial pressure | 1.5 bar | 1.5 bar |
| feed time | 3 h 43 min | 3 h 47 min |
| Reaction temperature | 10–16° C. | 10–12° C. |
| Post reaction time | 2 h | 2 h |
| $CH_3COOH$ amount | 92.7 kg | 92.9 kg |
| Ester/ketone ratio | 16.7:1 | 17.8:1 |

EXAMPLE 5

A 4 liter glass lined reactor, equipped with a hollow shaft mixer, capable of transferring the gas phase effectively into the liquid phase, was charged with 500 g sodium methoxide and 2502 g recycled dimethyl carbonate. The dimethyl carbonate was recycled from previous batches by fractionated distillation and used without further purification. After flushing with nitrogen, the reactor was evacuated and the mixer was started. 926 g of TFE were fed to the reactor at 10° C. over a period of 3 h 38 min. The partial pressure of TFE was 1.2 bar. After a post reaction time of 2 h 340 g of gaseous HCl were added to the batch at 30 to 40° C. The mixture was stirred for 2 h at 30° C. and worked up by filtration. The ester/ketone ratio was 11.7:1.

EXAMPLE 6

Example 5 was repeated, but the recycled dimethyl carbonate was deliberately contaminated with 5 weight % of methyl 3-methoxy perfluoropropionate. After work up, the resulting ester/ketone ratio was 15:1.

The example demonstrates that the presence of methyl 3-methoxy perfluoropropionate in the recycled diester does not have an adverse effect on the desired reaction.

What is claimed is:
1. Process for preparing a desired halogenated ester, said process comprising the steps of:
(a) contacting (A) a substantially organic solvent free liquid mixture of (i) an alkanolate of the formula M—O—Z, wherein M is an alkali or alkaline earth metal, and Z is a linear, branched or cyclic alkyl group of 1 to 10 carbon atoms and (ii) a diester with (B) a halogenated ethylenically unsaturated olefin at a temperature of not more than 40° C. and with a mol ratio of halogenated ethylenically unsaturated olefin to alkanolate of not more than 1.1;

(b) contacting an acid with a thus obtained reaction mixture thereby obtaining a mixture comprising the desired halogenated ester;

(c) recovering said halogenated ester from said reaction mixture, and wherein in step (a) said mixture of said alkanolate and diester is contacted with said halogenated ethylenically unsaturated olefin under conditions of agitation sufficient such that the weight ratio of halogenated ester to halogenated ketone as a byproduct obtained after step (b) is at least 10:1.

2. Process according to claim 1 wherein said mol ratio of halogenated ethylenically unsaturated olefin to alkanolate is between 0.9 and 1.1.

3. Process according to claim 1 or 2 wherein said diester is dimethyl carbonate and said alkanolate is a methanolate.

4. Process according to claim 1 wherein said halogenated ethylenically unsaturated olefin is tetrafluoroethylene.

5. Process according to claim 1 wherein step (a) is carried out at a temperature between 4 and 40° C.

6. Process according to claim 1 wherein steps (a) to (c) of the process are conducted without adding organic solvent.

7. Process according to claim 1 wherein said diester is recovered from said reaction mixture obtained after said step (b).

8. Process according to claim 7 wherein said recovered diester is reused in a process according to claim 1.

9. Process of utilizing a halogenated ester obtained by the process of claim 1 in the manufacture of a fluorinated vinyl ether.

10. Process for preparing a fluorinated vinyl ether comprising the steps of:

(a) contacting (A) a substantially organic solvent free liquid mixture of (i) an alkanolate of the formula M—O—Z, wherein M is an alkali or alkaline earth metal, and Z is a linear, branched or cyclic alkyl group of 1 to 10 carbon atoms and (ii) a diester with (B) a halogenated ethylenically unsaturated olefin at a temperature of not more than 40° C. and with a mol ratio of halogenated ethylenically unsaturated olefin to alkanolate of not more than 1.1;

(b) contacting an acid with a thus obtained reaction mixture thereby obtaining a mixture comprising the desired halogenated ester;

(c) recovering said halogenated ester from said reaction mixture, wherein in step (a) said mixture of said alkanolate and diester is contacted with said halogenated ethylenically unsaturated olefin under conditions of agitation sufficient such that the weight ratio of halogenated ester to halogenated ketone as a byproduct obtained after step (b) is at least 10:1;

(d) converting the mixture of step (b) to an acid fluoride by fluorination; and (e) converting the acid fluoride to a vinyl ether.

* * * * *

UNITED STATES PATENT AND TRADEMARK OFFICE
CERTIFICATE OF CORRECTION

PATENT NO. : 6,703,520 B2
DATED : March 9, 2004
INVENTOR(S) : Hintzer, Klaus

It is certified that error appears in the above-identified patent and that said Letters Patent is hereby corrected as shown below:

Column 10,
Lines 1-2, "of utilizing a halogenated ester obtained by the process of claim 1" should be replaced with -- according to claim 1, further comprising employing the halogenated ester --

Signed and Sealed this

Twenty-first Day of September, 2004

JON W. DUDAS
*Director of the United States Patent and Trademark Office*